United States Patent [19]

Toriya et al.

[11] 4,057,472
[45] Nov. 8, 1977

[54] METHOD OF SEPARATING DIACETOXYBUTENE

[75] Inventors: Jun Toriya; Masato Sato; Ken Shiraga; Setsuo Matsunaga; Noboru Haji, all of Kurashiki, Japan

[73] Assignees: Mitsubishi Chemical Industries Ltd., Tokyo, Japan

[21] Appl. No.: 656,011

[22] Filed: Feb. 6, 1976

Related U.S. Application Data

[63] Continuation-in-part of Ser. No. 557,260, March 11, 1975, abandoned.

[30] Foreign Application Priority Data

Mar. 12, 1974 Japan .................. 49-28413

[51] Int. Cl.$^2$ .................. C07C 69/02; B01D 3/10
[52] U.S. Cl. .................. 203/80; 203/14; 560/244
[58] Field of Search .......... 260/497 A, 497 R, 488 H, 260/485 S, 499 V; 203/73, 80, 91, 14

[56] References Cited

U.S. PATENT DOCUMENTS

| | | | |
|---|---|---|---|
| 3,188,354 | 6/1965 | Roming | 203/80 |
| 3,329,586 | 7/1967 | Pettingill | 203/80 |
| 3,513,078 | 5/1970 | Biarnais et al. | 203/80 |
| 3,658,659 | 4/1972 | Cottle | 203/79 |
| 3,671,577 | 6/1972 | Ono et al. | 260/497 A |
| 3,872,163 | 3/1975 | Shimizu et al. | 260/497 A |

*Primary Examiner*—Wilbur L. Bascomb, Jr.
*Attorney, Agent, or Firm*—Oblon, Fisher, Spivak, McClelland & Maier

[57] ABSTRACT

A fractional distillation method of separating diacetoxybutene isomers from a reaction mixture produced from the reaction of butadiene, acetic acid and molecular oxygen comprises employing a series of at least two distillation towers, one of said towers being used for distillation of water and acetic acid under a pressure of 30 – 250 Torr and a tower bottom temperature of 190° – 120° C and the other being used for separation of high boiling point materials under a pressure of 2 – 100 Torr and a tower bottom temperature of 190° – 120° C, the temperature of all tower bottoms being from 190° – 120° C.

4 Claims, 1 Drawing Figure

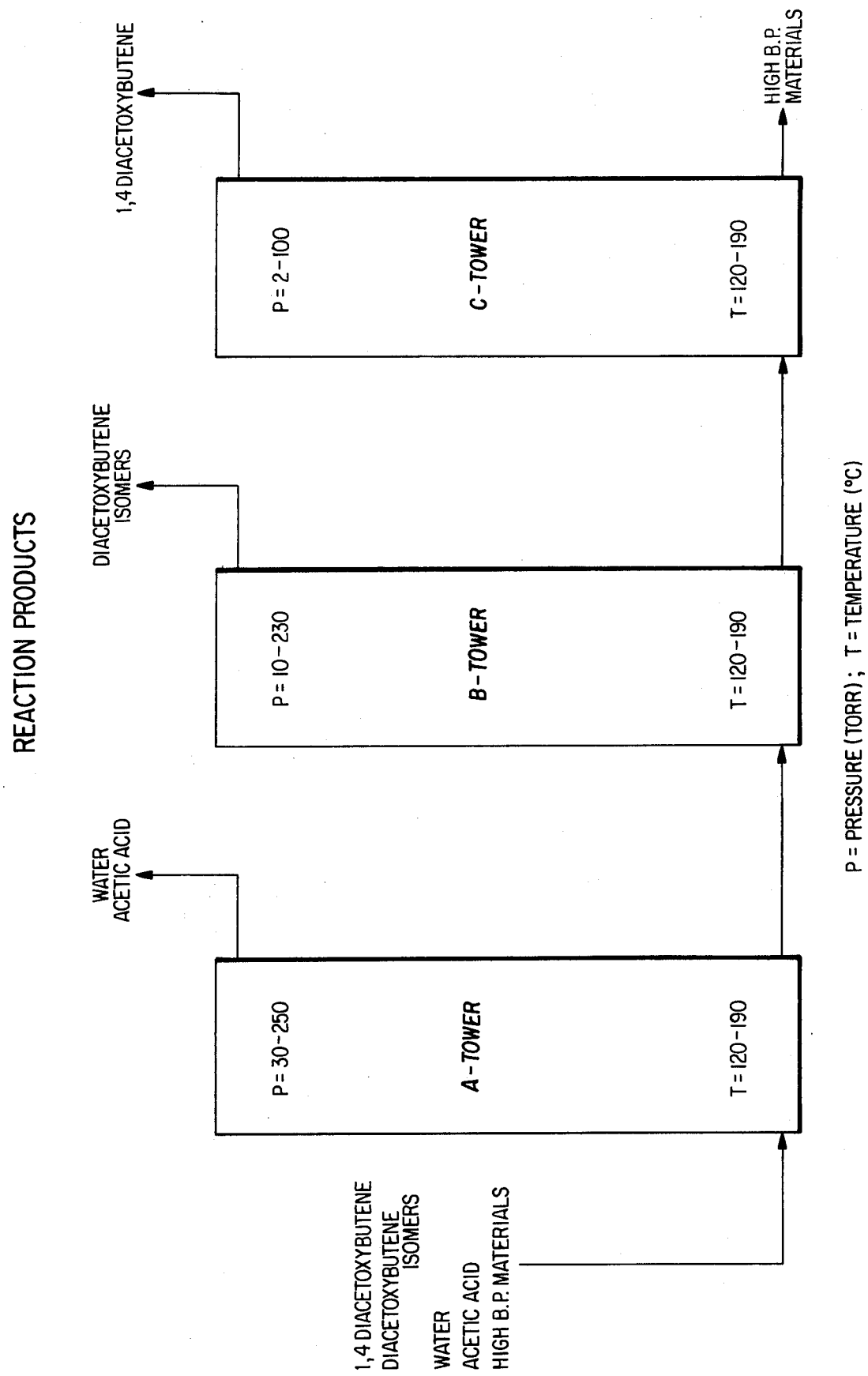

METHOD OF SEPARATING DIACETOXYBUTENE

CROSS-REFERENCE TO RELATED APPLICATION

This application is a continuation-in-part of U.S. patent application Ser. No. 557,260, filed on Mar. 11, 1975, now abandoned.

BACKGROUND OF THE INVENTION

1. Field of the Invention

The present invention relates to a method of separating diacetoxybutene. More particularly, it relates to a method separating diacetoxybutene from a reaction product resulting from the reaction of butadiene, acetic acid and molecular oxygen.

2. Description of the Prior Art

Diacetoxybutene is an important starting material for producing butanediol which is an important solvent and raw material for various industrial chemicals. Various methods of producing diacetoxybutene have been proposed. A typical method has been the reaction of butadiene, acetic acid and oxygen or an oxygen-containing gas in the presence of a palladium-type catalyst. It is necessary to separate diacetoxybutene from the reaction mixture resulting from this acetoxylation reaction. However, since both the unreacted starting material and the object compound, diacetoxybutene, have unsaturated radicals, polymerization of these compounds occurs quite readily when using separation treatments. Product yield is therefore decreased and operation problems result. The inventors have studied various methods of separating diacetoxybutenes from the reaction mixture of the acetoxylation reaction. As a result, it has been discovered that diacetoxybutenes are easily decomposed or polymerized at higher than a certain specific temperature but are relatively stable at lower than a certain temperature.

SUMMARY OF THE INVENTION

Accordingly, it is an object of this invention to provide a method of separating diacetoxybutenes from the reaction mixture of the acetoxylation reaction in high yield and with trouble-free operation.

Briefly, this and other objects of the invention, as hereinafter will become apparent, are achieved by providing a method of separating diacetoxybutene from a reaction mixture produced by reacting butadiene, acetic acid, and molecular oxygen in the presence of a palladium-type catalyst, which comprises maintaining the temperature of the distillation tower bottoms at lower than 190° C while controlling the pressure within the distillation tower.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a flow diagram of a preferred embodiment of the process of this invention.

DETAILED DESCRIPTION OF THE PREFERRED EMBODIMENTS

The reaction mixture used for this invention is produced by an acetoxylation process in which butadiene, acetic acid and molecular oxygen are reacted in the presence of a palladium-type catalyst. The acetoxylation reaction producing such reaction mixture is conducted by known methods. Butadiene used as a starting material for the acetoxylation reaction can be a pure compound or a mixture of butadiene and other saturated hydrocarbons such as methane, ethane, butane, etc. While anhydrous acetic acid is preferably used as the other starting material, other forms of this material are also acceptable for the acetoxylation. The catalyst used for the reaction is preferably a supported palladium metal catalyst or palladium metal and at least one promoter metal such as bismuth, selenium, antimony or tellurium on a carrier, such as magnesia, diatomaceous earth, pumice, etc. The amount of the catalytic metal in the catalyst is usually 0.1 – 20 wt. % of palladium metal and 0.01 – 30 wt. % of the promoter metal. The reaction can be conducted in any desirable system such as a fixed bed system, a fluidized bed system, a suspending catalyst system and the like. The molecular oxygen fed into the reaction system is not limited to pure oxygen but can be diluted with an inert gas such as air. The reaction can be conducted at 40° – 180° C, preferably 60° – 150° C under a pressure higher than atmospheric pressure. The resulting acetoxylation reaction mixture contains unreacted butadiene, etc. Accordingly, it is preferable to use this reaction mixture after removing butadiene along with other impurities having boiling points similar to the boiling point of butadiene by a degasification process. After degasification, the reaction mixture contains 1,4-diacetoxybutene, diacetoxybutene isomers, water, acetic acid and high boiling point materials. Since the amount of these materials remaining in the reaction mixture is dependent upon the reaction conditions it is relatively difficult to define their exact quantity. However, it can be estimated that the amount of butadiene derivatives, including diacetoxybutenes and high boiling point materials may be 0.5 – 50 wt. %, and the amount of water may be 0.05 – 20 wt. %. The amounts of diacetoxybutenes in the butadiene derivative may be from 50 – 95 wt. % 1,4-diacetoxybutene; from 5 – 45 wt. % of isomers of diacetoxybutene and from 0.1 – 10 wt. % of high boiling point materials. The reaction mixture is distilled in accordance with the method of this invention. For such distillation it is preferable to employ a series of plural distillation towers. For example, when isomeric diacetoxybutenes are separated, a distillation tower for water and acetic acid (referred to as the A-tower) and a distillation tower for high boiling point materials (referred to as the C-tower) are employed in the alternate arrangements of A-C or C-A. Thus, it is preferable to dispose the towers in an A-C arrangement because the high boiling point materials produced in the distillation can be separated to a much higher degree. When 1,4-diacetoxybutene is separated, it is customary to employ a distillation tower for isomers of diacetoxybutene (referred to as the B-tower). In this case, it is possible to dispose the towers in an A-B-C, a C-A-B or an A-C-B arrangement. It is preferable to operate in an A-B-C arrangement as illustrated in FIG. 1. Further, it is possible to employ both an atmospheric pressure tower and a reduced pressure tower as the A-tower. In the distillation process of this invention, it is necessary to maintain the temperature of all tower bottoms at lower than 190° C, since the thermal stability of the diacetoxybutene-containing reaction mixture is remarkably decreased at higher than this temperature as disclosed in Table 1. The boiling point of 1,4-diacetoxybutene-2 is 222° – 230° C at atmospheric pressure and the boiling point of 3,4-diacetoxybutene-1 is 206° – 208° C at atmospheric pressure. under reduced pressure, these compounds can be separated by fractionation at lower than 190° C. However, the separation of the cis- and trans-compounds does not occur readily.

In the A-tower, water and acetic acid are distilled from the top of the tower and the diacetoxybutenes remain in the bottom. In the C-tower, diacetoxybutenes (or separated 1,4-diacetoxybutene-2) are distilled, with the remaining high boiling point materials being held at the bottom of the tower. The distillations are conducted under suitable reduced pressures and the temperature of the tower bottoms is maintained at lower than 190° C, usually at 120° – 190° C, preferably 140° – 180° C.

Having generally described the invention, a further understanding can be obtained by certain specific examples which are provided herein for purposes of illustration only and are not intended to be limiting in any manner.

The reduced pressure conditions at the tops of the towers (referred to as the operation pressure) are shown in Table 1.

TABLE 1

| | Pressure conditions at the top of the distillation towers (Torr) | |
|---|---|---|
| | Usual Range | Preferable Range |
| A-tower | 30–250 | 30–150 |
| B-tower | 10–230 | 10–100 |
| C-tower | 2–100 | 5–50 |

EXAMPLE 1

A condenser made of Pyrex glass in which is inserted a thermometer for measuring the inner temperature is connected to a three necked flask made of Pyrex glass having a volume of 300 ml. A tube supplying nitrogen gas is connected to the top of the condenser. 150g of the diacetoxybutene-containing solution having the formulation shown below was charged into the flask. The vessel was swept with nitrogen so as to remove any air and then sealed. The flask was heated by means of a heat transfer medium to those temperatures shown in Table 2 and maintained at those temperatures for 10 hours. After cooling to room temperature, the contents were sampled and analyzed by gas chromatography.

| Formulation of Sample | |
|---|---|
| Sample I: | wt. % |
| 1,4-diacetoxybutene-2 | 79.6 |
| 3,4-diacetoxybutene-1 | 10.2 |
| acetic acid | 8.2 |
| other components | 2.0 |
| Sample II: | wt. % |
| 1,4-diacetoxybutene-2 | 98.5 |
| other components | 1.5 |

TABLE 2

The effect of temperature on the amount of diacetoxybutene isomers remaining after distillation

| Temperature | 180° C | 200° C | 210 – 232° C |
|---|---|---|---|
| Temperature of the heat transfer medium | 191 – 193 | 211 – 213 | 250 – 260 |
| Sample I | 99.8% | 99.0% | 85.0% |
| Sample II | 99.6% | — | 94.0% |

In table 2, the ratio of the amount of diacetoxybutene isomers remaining in the sample after heating to the distillation temperature relative to the amount of diacetoxybutene isomers in the sample before heating (X100%) is shown. As can be seen from Table 2, when the temperature of the distillation tower bottom is higher than 190° C, the production of low boiling point materials results from the decomposition of diacetoxybutenes. Further, the production of high boiling point materials also occurs from the polymerization of diacetoxybutenes. The distillation loss of diacetoxybutenes is therefore remarkably high and economically disadvantageous. In addition, it is difficult to maintain a stable distillation operation since the production of low boiling point materials and the adhesion of the high boiling point materials to the heating surface destroys equilibrium conditions so necessary for successful distillation. When the amount of high boiling point materials is increased, it is necessary to increase the temperature of the tower bottom in order to effectively distill the diacetoxybutenes. However, at higher temperatures the further production of high boiling point materials is disadvantageously promoted and with an attendant loss of diacetoxybutenes. Thus, it is necessary to maintain the tower bottom at temperatures lower than 190° C and preferably at 190° – 120° C. In order to achieve a successful distillation at lower than 120° C, the operating pressure within the tower must be lower than 10 Torr which is disadvantageous for an industrial operation. Also, the temperature of the tower top is low, whereby acetic acid and 1,4-diacetoxybutene may condense before the condenser and not be collected as distillate. As operating conditions for the distillation tower, the temperature of the tower bottoms should be from 120° – 190° C and the operation pressure 30 – 250 Torr in the A-tower; 10 – 230 Torr in the B-tower; and 2 – 100 Torr in the C-tower. However, it is possible to operate outside these ranges. For example, atmospheric pressure may be used in the A-tower so as to cause an increase in the concentration of diacetoxybutene. As stated above, in accordance with the method of this invention, the temperature of the tower bottoms is maintained at lower than a specific temperature during the distillation of the acetoxylation reaction mixture, thereby minimizing side-reactions of decomposition or polymerization and effectively obtaining the object diacetoxybutenes.

EXAMPLE 2

A sieve-tray distillation tower made of glass and having 13 plates was used as the A-tower. A sieve-tray distillation tower made of glass and having 25 plates was used as the C-tower. An acetoxylation reaction mixture was continuously distilled under the conditions shown in Table 3 so as to obtain diacetoxybutenes in a yield of 98%. The acetoxylation reaction mixture was produced by reacting butadiene, acetic acid and oxygen in the presence of a catalyst comprising palladium and antimony on activated carbon (10 m mol Pd/100 g activated cabon and 3 m mol Sb/100 g activated carbon). The mixture contained 36.3 wt. % of diacetoxybutenes, 0.7 wt. % of high boiling point materials with the remainder being acetic acid with small amounts of low boiling point impurities.

TABLE 3

| OPERATING CONDITIONS | | |
|---|---|---|
| | A-tower | C-tower |
| Temperature of tower bottom | 158 – 162° C | 177 – 182° C |
| Operating pressure, tower top | 74 Torr | 70 Torr |

TABLE 3-continued

| | OPERATING CONDITIONS | |
|---|---|---|
| | A-tower | C-tower |
| Residence time, tower bottom | about 2 hours | about 10 hours |
| Ratio of recycling | 0.5 | 1.0 |

REFERENCE

The same acetoxylation reaction mixture was continuously distilled under the conditions shown in Table 4 by employing the same distillation towers as used in Example 2. The resulting diacetoxybutenes discharged from the tower bottom of A-tower were severely colored and very viscous. Accordingly, the operation of the C-tower was quite difficult. The yield of diacetoxybutenes was only 54% as compared to 98% from Example 2.

TABLE 4

| | OPERATING CONDITIONS | |
|---|---|---|
| | A-tower | C-tower |
| Temperature of tower bottom | 215 – 225° C | 190 – 200° C |
| Operation pressure tower top | 420 Torr | 135 Torr |
| Resident time tower bottom | about 2 hours | about 2 hours |
| Ratio of recycling | 0.5 | 1.0 |

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A fractional distillation method of separating diacetoxybutent isomers from a reaction mixture, produced from the reaction of butadiene, acetic acid and molecular oxygen which comprises employing a series of two distillation towers, feeding said reaction mixture into the first tower to distill away water and acetic acid under a pressure of 30 – 250 Torr and a tower bottom temperature within the range of from 120° C to less than 190° C, withdrawing the material remaining in the bottom of the first tower and then feeding said material into the second tower to separate diacetoxybutene from high boiling point materials under a pressure of 2 – 100 Torr and a tower bottom temperature within the range of from 120° C to less than 190° C.

2. the method of claim 1, wherein the pressure of the first tower is 30 – 150 Torr and that of the second is 5 – 50 Torr.

3. The method of claim 1, wherein the bottom temperature of both towers is from 140° to 180° C.

4. The method of claim 1, wherein the reaction mixture has been degassed prior to distillation.

* * * * *